United States Patent [19]

Parker

[11] Patent Number: 5,177,243
[45] Date of Patent: Jan. 5, 1993

[54] N,N'-DIACETIC ACID-N'-CYANOMETHYL, SALTS THEREOF, AND THEIR PREPARATION

[75] Inventor: Brian A. Parker, Nashua, N.H.

[73] Assignee: W.R. Grace & Co.-Conn., New York, N.Y.

[21] Appl. No.: 806,032

[22] Filed: Dec. 21, 1991

[51] Int. Cl.$^5$ .......................................... C07C 255/00
[52] U.S. Cl. .................................................. 558/442
[58] Field of Search ........................................ 558/442

[56] References Cited

PUBLICATIONS

CA 114:117859a Chelants . . . , thereof. Wilson et al., p. 362, 1991.

Primary Examiner—Mary C. Lee
Assistant Examiner—Joseph K. McKane
Attorney, Agent, or Firm—Kevin S. Lemack; William L. Baker

[57] ABSTRACT

A novel intermediate useful in the synthesis of ethylenediaminetriacetic acid (ED3A) or its salts. A salt of N,N'-ethylenediaminediacetic acid (ED2AH$_2$) is condensed with formaldehyde to form a stable 5-membered ring intermediate. The addition of cyanide across this cyclic material forms ethylenediamine N,N'-diacetic acid-N'-cyanomethyl or salts thereof (mononitrilediacid), which is useful intermediate in the production of ED3A. The nitrile in aqueous solutions may be spontaneously cyclized to form 2-oxo-1,4-piperazindeiacetic acid (3KP) or salts thereof. In the presence of excess base, salts of ED3A are formed in excellent yield and purity.

1 Claim, No Drawings

N,N'-DIACETIC ACID-N'-CYANOMETHYL, SALTS THEREOF, AND THEIR PREPARATION

BACKGROUND OF THE INVENTION

Ethylenediaminetriacetic acid (ED3A) or its salts (such as ED3ANa$_3$) has application in the field of chelating chemistry, and may be sued as a starting material in the preparation of strong chelating polymers, oil soluble chelants, surfactants an others. Conventional routes for the synthesis of ethylenediaminetriacetic acid were achieved via its N-benzyl derivative, which was subsequently hydrolyzed in alkaline solutions to ED3ANa$_3$, thus avoiding cyclization to its 2-oxo-1,4-piperazinediacetic acid (3KP) derivative. Syntheses attempted by both the alkaline condensation of chloroacetic acid with ethylenediamine, and the carboxymethylation of the diamine with formaldehyde and sodium cyanide resulted in complex mixtures requiring complex extraction techniques (e.g. almost exclusive solubility of 3KP in boiling dimethylformamide, Can. J. chemistry 1970, 48(1), 163–175) to generate the desired product, and then in only relatively poor yield. In addition, conventional processes resulted in large quantities of by-product, such as ethylenediaminetetraacetic acid (ed4A). Where the by-products were especially objectionable, complicated blocking techniques were necessary in order to achieve a relatively pure solution.

One example of the synthesis of ethylenediamine-N,N,N'-triacetic acid is shown in *Chemical Abstracts 78*, Vol. 71, page 451, no. 18369c, 1969. There it is disclosed that ethylenediamine reacts with ClH$_2$CCO$_2$H in a 1:3 molar ratio in basic solution at 10° C. for 24 hours to form a mixture from which ethylenediamine-N,N,N'-triacetic acid can be separated by complexing the same with Co(III). The resulting cobalt complexes can be isolated through ion exchange.

The instant invention is directed to a novel composition of matter that is useful as an intermediate in the synthesis of ethylenediaminetriacetic acid or its salts in high conversions and excellent yield.

SUMMARY OF THE INVENTION

The problems of the prior art have been overcome by the instant invention, which provides a novel composition of matter useful as an intermediate in the synthesis of ethylenediaminetriacetic acid. Specifically, a mononitrile-diacid is formed by reacting a salt of N,N'-ethylenediaminediacetic acid (ED2AH$_2$) with formaldehyde to form a stable 5- membered ring intermediate. The addition of cyanide across this cyclic material forms ethylenediamine N,N'-diacetic acid-N'-cyanomethyl or salt there of (the mononitrile-diacid). This nitrile in aqueous solution may be spontaneously cyclized to form 3KP or salts thereof, which in the presence of excess base, forms salts of ED3A in excellent yield and purity.

DETAILED DESCRIPTION OF THE INVENTION

Suitable salts of ethylenediaminediacetic acid useful as the starting material in the instant invention include alkali and alkaline earth metal salts, in particular, the sodium and potassium salts. For purposes of illustration, the sodium salt will be used, although it should be understood that other salts may be employed without departing from the spirit and scope of the invention. One suitable reaction scheme of the synthesis of the mononitrile-diacid is the alkaline condensation of formaldehyde with N,N'-ethylenediamine disodium acetate to form a 5-membered ring structure, 1,3-bis(carboxymethyl)imidazolidine, and is illustrated as follows:

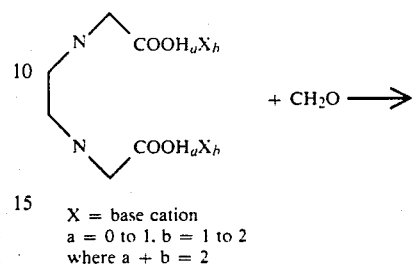

X = base cation
a = 0 to 1, b = 1 to 2
where a + b = 2

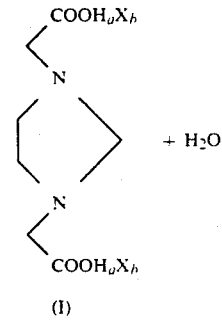

The above reaction may be carried out in the presence of additional base. Suitable bases include alkali and alkaline earth metal hydroxides, preferably sodium and potassium hydroxide. Compound (I) is the bridged reaction product of EDDANa$_{(1.0\rightarrow2.0)}$ and formaldehyde, which the present inventor has found to be a stable intermediate in the ED3A synthesis. Compound (I) is formed easily between 0° and 110° C. The reaction proceeds quickly and forms readily at pH's greater than about 7.0. Preferably the temperature employed is about 0° to 65° C., most preferably 15° to 65° C., although temperatures higher than 65° C. are operable. Formaldehyde can be used in stoichiometric amounts, although it is preferred that a slight molar excess be used, preferably 0.5%–2.0%. Preferably the concentration of the formaldehyde is 55% or less in aqueous solution. Paraformaldehyde also can be used.

The second step in the reaction scheme is illustrated below:

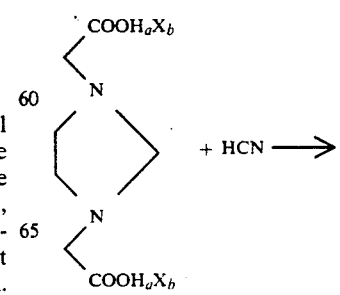

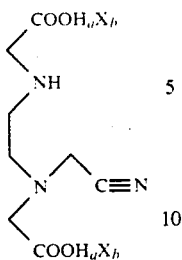

(II) Mononitrile-diacid

Compound (II) is readily formed at temperatures between 0° and 110° C. The reaction should be conducted at temperatures at or below the boiling point of the solution. Preferably the reaction is carried out at temperatures from about 0° to about 65° C., most preferably about 15° to 65° C. to enhance the reaction rate. Suitable sources of cyanide include gaseous hydrogen cyanide, and aqueous solution of hydrogen cyanide, or alkali metal cyanide such as sodium cyanide or potassium cyanide, etc. The cyanide may be used in stoichiometric amounts, although slight molar excesses may be used, preferably 0.5%-2.0%.

Compound (II) is useful as an intermediate for the production of ED3A. Specifically, compound (II) maybe hydrolyzed to the monoamide-diacid compound (III) (partially hydrolyzed mononitrile diacid), which spontaneously cyclized to 3KP. Compound (IV) forms readily in the presence of a base such as alkali metal or alkaline earth metal hydroxides. Preferably the base is NaOH. Mole rations of <3.0 M base :1 M ED2AH$_2$ but preferably <2.0 M base:1 M ED2AH$_2$ are employed. Higher concentrations of base (i.e. >3.0 M base:M ED2AH$_2$) cause some disproportionation of the diacid mononitrile and some ED4A (ethylenediaminetetraacetic acid) is formed, especially at temperatures >65° C. In particular, the concentration of ED4A is found to e in direct proportion to the amount of excess caustic employed, when high temperature reactions are conducted and high molar ratios of base are employed (>2.0 M base:1 M ED2AH$_2$), which may be attributed to the simultaneous hydrolysis of 3KP and disproportionation of the mononitrile-diacid. When the mole ratio of base to ED2A is <2.0, higher temperatures may be used. Also, in Step III ammonia is eliminated between an amide group and an imino group on the same molecule. However, at lower temperatures (<65° C.) higher amounts of base may be employed (>2.0 M) and hydrolysis of compound (II) can proceed directly to ED3A without cyclization.

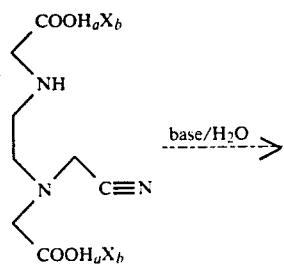

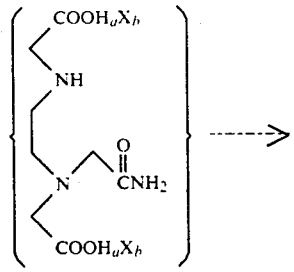

(III)

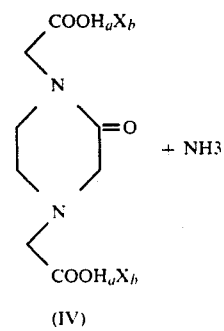

(IV)

The 3KPNa$_2$ is then hydrolyzed by at least the addition of 1 equivalent of caustic, preferably a 1 molar excess of caustic. This amounts to approximately 5% weight excess (free) caustic in solution on a 40% ED-3ANa$_3$ solution. The solution is boiled under atmospheric pressure to the desired concentration. Preferably the reaction is carried out by raising the temperature from the temperature in the formation of compound (IV) reaction to the boil over a period from about 30 minutes to bout 6 hours.

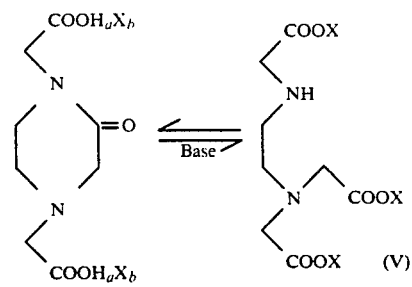

X = base cation

The resulting solution typically give approximately 35-40% ED3ANa$_3$, with approximately 2% 3KPNa$_2$ remaining as an unopened ringed structure. This corresponds to about a 94% conversion to ED3ANa$_3$, with the remaining 6% of mass existing as 3KPNa$_2$. Acidification of this mass to pH's <6.0 to produce ED3AH$_3$ is not possible, as cyclization to 3KPH$_2$ will eventually occur.

The foregoing synthetic scheme results in conversions to ED3ANa$_3$ in excess of 90%, with the residual proportion being 3KPNa$_2$ to give a total mass balance of virtually 100%. The reactions are tolerant to wide pH range.

The following procedure to obtain ED2AH$_2$ was for experimental purposes only. Far less elaborate schemes for the production of ED2AH₂ are possible. Any schemes know in the art can be employed for the production of ED2AH₂ and its salts, and the instant invention is not to be limited by any particular scheme.

In the following examples, all batches were synthesized from EDDAH₂ (98.20%) obtained by acidification of EDDANa₂ to a pH of 5.50 with nitric acid, while maintaining the temperature of the solution <10° C. The resultant slurry was filtered by means of a Buchner funnel with the vacuum provided by a water aspirator. The filter cake was washed with approximately 7 liters of iced H₂O. To enhance drying, the cake was then washed with approximately 1 liter of MeOH. The crystals were then placed on 1 inch deep stainless steel trays, dried in a Stockes vacuum dryer, model 338F at 40 °C. under a vacuum of 4 mm Hg, for 12 hours. Approximately 2 Kg of a white crystalline powder was recovered. Analysis of this powder showed it to be 98.2% ED2AH₂.

All batches were synthesized on a 0.5 liter scale. 88 g of ED2AH₂ were charged to a 500 ml conical flask and diluted with 180 mls of H₂O. 50% caustic was used to obtain the sodium salt in the ratio required. This solution was stirred for 30 minutes, and then charged to a 1 liter 5-necked round bottom flask. The conical flask was then washed with 20 mls. of H₂O, and the washing transferred to the round bottom flask. The ground bottom flask was equipped with a magnetic stirring bar, a condenser (ethylene glycol/H₂O @ 0° C.), A 0°-150° C. mercury thermometer, and a J-type thermocouple that provided a signal to a Love proportional controller, which maintained the temperature at the desired level were employed. A glass-Col heating mantle controlled by the Love controller via a Powerstat variable autotransformer was used to heat the contents of the flask. 37% CH₂O and 100% HCN were pumped at approximately 1 g/minute and 0.50 g/minute, respectively, by an FMI micro metering pump at a setting of 0.5, via ⅛" Teflon tubing to the flask. A 125 ml addition funnel equipped with a teflon metering valve, and a condenser with the same coolant as described above, was used as the reservoir for the reactants to be pumped. Table 1 shows the results for the experiments conducted up to the spontaneous cyclization of monoamide-diacid after it has been hydrolyzed. The mononitrile-diacid was not isolated; however, it was identified by HPLC as being the precursor to 3KP. 3KP. was more easily quantified by HPLC, and its is that compound which si quantitatively shown in Table 1. Table 2 shows results for ED3A produced for 9 conditions using the compound of the instant invention.

TABLE 1

| Exp | Tot wt | Comments | temp | t (mins) | Moles EDDA | Ic % EDDANa2 | Ic % ED3ANa3 | Ic % 3KPNa2 | % EDDA to Produc | % Unrxl EDDA | Mass balance |
|---|---|---|---|---|---|---|---|---|---|---|---|
| | | | | | | 220.00 | 300.00 | 260.00 | | | |
| 1 - 0 | 240.75 | 2NaOH/1EDDA | 50 | 0.0 | 0.247 | 22.57% | 0.00% | 0.00% | 0.00% | 100.00% | 100.00% |
| 1 - 1 | 238.98 | 50° C. | 50 | 55.0 | 0.245 | 4.36% | 0.30% | 11.68% | 44.76% | 19.32% | 64.08% |
| 1 - 2 | 234.04 | | 50 | 102.0 | 0.240 | 3.03% | 0.50% | 15.15% | 58.42% | 13.42% | 71.84% |
| 1 - 3 | 228.13 | | 50 | 144.0 | 0.234 | 2.13% | 0.60% | 17.50% | 67.55% | 9.44% | 76.99% |
| 1 - 4 | 221.69 | | 50 | 199.0 | 0.227 | 1.51% | | 19.21% | 72.02% | 6.69% | 78.71% |
| 1 - 5 | 214.52 | | 50 | 250.0 | 0.220 | 1.14% | | 20.54% | 77.00% | 5.05% | 82.05% |
| 1 - 6 | 208.17 | | 50 | 300.0 | 0.214 | 0.89% | 1.20% | 20.90% | 82.25% | 3.94% | 86.19% |
| final sc | 202.88 | | | | | | | | | | |
| 2 - 0 | 240.75 | 2NaOH/1EDDA | 65 | 0.0 | 0.247 | 22.57% | | 0.00% | 0.00% | 100.00% | 100.00% |
| 2 - 1 | 240.75 | 65° C. | 65 | 15.0 | 0.247 | 3.84% | | 13.94% | 52.26% | 17.01% | 69.27% |
| 2 - 2 | 236.21 | | 65 | 45.0 | 0.242 | 2.58% | | 17.68% | 66.28% | 11.43% | 77.71% |
| 2 - 3 | 231.19 | | 65 | 90.0 | 0.237 | 1.49% | | 20.89% | 78.31% | 6.60% | 84.91% |
| 2 - 4 | 226.19 | | 65 | 135.0 | 0.232 | 1.45% | | 21.64% | 81.12% | 6.42% | 87.55% |
| 2 - 5 | 220.81 | | 65 | 186.0 | 0.227 | 1.41% | | 21.81% | 81.76% | 6.25% | 88.01% |
| 2 - 6 | 214.61 | | 65 | 230.0 | 0.220 | 1.36% | | 21.73% | 81.46% | 6.03% | 87.49% |
| 2 - 7 | 210.35 | | 65 | 262.0 | 0.216 | 1.28% | | 21.74% | 81.50% | 5.67% | 87.17% |
| 2 - 8 | 205.04 | | 65 | 990.0 | 0.211 | 1.23% | | 21.60% | 80.97% | 5.45% | 86.42% |
| final sc | 197.00 | | 65 | | | | | | | | |
| 3 - 0 | 240.75 | 2NaOH/1EDDA | 90 | 0.0 | 0.247 | 22.57% | | 0.00% | 0.00% | 100.00% | 100.00% |
| 3 - 1 | 239.86 | 80° C. | 80 | 10.0 | 0.246 | 4.16% | | 15.92% | 59.68% | 18.43% | 78.11% |
| 3 - 2 | 235.19 | | 80 | 35.0 | 0.241 | 3.66% | | 18.66% | 69.95% | 16.22% | 86.17% |
| 3 - 3 | 229.91 | | 80 | 75.0 | 0.236 | 3.33% | | 19.61% | 73.51% | 14.75% | 88.27% |
| 3 - 4 | 223.28 | | 80 | 136.0 | 0.229 | 3.04% | | 19.50% | 73.10% | 13.47% | 86.57% |
| 3 - 5 | 217.66 | | 80 | 210.0 | 0.223 | 2.89% | | 19.77% | 74.11% | 12.80% | 86.92% |
| 3 - 6 | 211.34 | | 80 | 280.0 | 0.217 | 2.69% | | 19.99% | 74.94% | 11.92% | 86.86% |
| final sc | 205.07 | | 80 | | | | | | | | |
| 4 - 0 | 239.10 | 1.9NaOH/1EDDA | 50 | 0.0 | 0.247 | 22.73% | | 0.00% | 0.00% | 100.00% | 100.00% |
| 4 - 1 | 239.10 | 50° C. | 50 | 30.0 | 0.247 | 6.73% | | 6.34% | 23.60% | 29.61% | 53.22% |
| 4 - 2 | 234.00 | 1.0 CH₂O | 50 | 70.0 | 0.242 | 5.00% | | 10.24% | 38.12% | 22.00% | 60.13% |
| 4 - 3 | 228.81 | | 50 | 115.0 | 0.236 | 4.18% | | 13.58% | 50.56% | 18.39% | 68.95% |
| 4 - 4 | 223.25 | | 50 | 165.0 | 0.231 | 2.68% | | 16.40% | 61.06% | 11.79% | 72.85% |
| 4 - 5 | 217.35 | | 50 | 200.0 | 0.225 | 2.16% | | 17.99% | 66.98% | 9.50% | 76.48% |
| 4 - 6 | 212.72 | | 50 | 250.0 | 0.220 | 1.52% | | 19.66% | 73.20% | 6.69% | 79.89% |
| 4 - 7 | 208.46 | | 50 | 285.0 | 0.215 | 1.14% | | 20.75% | 77.26% | 5.02% | 82.27% |
| 4 - 8 | 192.50 | | 50 | 1280.0 | 0.199 | 0.13% | 1.10% | 23.50% | 91.04% | 0.57% | 91.62% |
| final sc | 138.00 | | boiled | | 0.201 | 0.13% | | 32.75% | 86.36% | 0.41% | 86.77% |
| 5 - 0 | 241.10 | 2.1NaOH/1EDDA | 50 | 0 | 0.247 | 22.54% | 0.00% | 0.00% | 0.00% | 100.00% | 100.00% |
| 5 - 1 | 241.10 | 50° C. | 50 | 40.0 | 0.247 | 5.58% | 0.10% | 9.35% | 35.43% | 24.76% | 60.19% |
| 5 - 2 | 236.01 | 1.05 CH2O | 50 | 90.0 | 0.242 | 3.85% | 0.20% | 14.31% | 54.37% | 17.08% | 71.46% |
| 5 - 3 | 231.32 | | 50 | 138.0 | 0.237 | 2.75% | 0.50% | 17.20% | 66.20% | 12.20% | 78.40% |
| 5 - 4 | 225.41 | | 50 | 186.0 | 0.231 | 2.15% | 0.80% | 18.60% | 72.43% | 9.54% | 81.97% |
| 5 - 5 | 220.92 | | 50 | 228.0 | 0.226 | 1.71% | 1.00% | 19.41% | 76.12% | 7.59% | 83.71% |
| 5 - 6 | 216.39 | | 50 | 260.0 | 0.222 | 1.49% | 1.30% | 19.85% | 78.75% | 6.61% | 85.36% |
| 5 - 7 | 211.83 | | 50 | 1350.0 | 0.217 | 0.66% | 3.40% | 16.01% | 71.17% | 2.93% | 74.10% |
| final sc | 170.21 | | boiled | | 0.220 | 0.92% | 5.10% | 23.10% | 82.02% | 3.24% | 85.26% |

TABLE 1-continued

| Exp | Tot wt | Comments | temp | t (mins) | Moles EDDA | % EDDANa2 | % ED3ANa3 | % 3KPNa2 | % EDDA to Produc | % Unrxl EDDA | Mass balance |
|---|---|---|---|---|---|---|---|---|---|---|---|
| 5 - 0 | 239.10 | 1.9NaOH/1EDDA | 80 | 0.0 | 0.247 | 22.73% | | 0.00% | 0.00% | 100.00% | 100.00% |
| 5 - 1 | 239.10 | 80° C. | 80 | 15.0 | 0.247 | 3.61% | | 17.05% | 63.48% | 15.88% | 79.36% |
| 5 - 2 | 233.80 | 1.05 CH2O | 80 | 45.0 | 0.242 | 3.01% | | 18.70% | 69.62% | 13.24% | 82.87% |
| 5 - 3 | 229.09 | | 80 | 90.0 | 0.237 | 2.61% | | 19.78% | 73.64% | 11.48% | 85.13% |
| 5 - 4 | 222.74 | | 80 | 145.0 | 0.230 | 2.26% | | 20.36% | 75.80% | 9.94% | 85.75% |
| 5 - 5 | 217.86 | | 80 | 189.0 | 0.225 | 1.32% | | 20.11% | 74.87% | 5.81% | 80.68% |
| 5 - 6 | 213.47 | | 80 | 240.0 | 0.221 | 1.60% | | 18.26% | 67.98% | 7.04% | 75.02% |
| 5 - 7 | 208.33 | | 80 | 285.0 | 0.215 | 1.66% | | 21.35% | 79.49% | 7.30% | 86.79% |
| 5 - 8 | 203.47 | | 80 | 1282.0 | 0.210 | 0.40% | 0.10% | 20.90% | 78.14% | 1.76% | 79.90% |
| 5 - 9 | 157.60 | | boiled | | 0.213 | 0.60% | 0.50% | 27.75% | 80.30% | 2.02% | 82.32% |
| 6 - 0 | 241.10 | 2.1NaOH/1EDDA | 80 | 0.0 | 0.247 | 22.54% | 0.00% | 0.00% | 0.00% | 100.00% | 100.00% |
| 6 - 1 | 241.10 | 80° C. | 80 | 20.0 | 0.247 | 3.72% | 1.00% | 18.17% | 71.47% | 16.51% | 87.97% |
| 6 - 2 | 235.20 | 1.00 CH2O | 80 | 74.0 | 0.241 | 3.44% | 1.00% | 19.09% | 74.92% | 15.26% | 90.19% |
| 6 - 3 | 229.95 | | 80 | 110.0 | 0.236 | 3.47% | 1.00% | 19.15% | 75.15% | 15.40% | 90.54% |
| 6 - 4 | 225.49 | | 80 | 155.0 | 0.231 | 3.37% | 1.00% | 19.44% | 76.24% | 14.95% | 91.19% |
| 6 - 5 | 220.51 | | 80 | 200.0 | 0.226 | 3.14% | 1.00% | 19.06% | 74.81% | 13.93% | 88.74% |
| 6 - 6 | 215.06 | | 80 | 238.0 | 0.220 | 3.15% | 1.00% | 19.20% | 75.34% | 13.98% | 89.31% |
| 6 - 7 | 210.36 | | 80 | 286.0 | 0.216 | 3.06% | 1.00% | 18.81% | 73.87% | 13.58% | 87.45% |
| 6 - 8 | 204.01 | | 80 | 320.0 | 0.209 | 3.08% | 1.00% | 19.19% | 75.30% | 13.67% | 88.96% |
| 6 - 9 | 198.58 | | 80 | 1286.0 | 0.203 | 2.30% | 1.70% | 19.39% | 78.33% | 10.20% | 88.53% |
| 6 - 10 | 145.33 | | boiled | | 0.206 | 2.49% | 1.80% | 21.94% | 63.79% | 7.99% | 71.78% |
| 7 - 0 | 239.10 | 1.9NaOH/1EDDA | 80 | 0.0 | 0.247 | 22.73% | | 0.00% | 0.00% | 100.00% | 100.00% |
| 7 - 1 | 239.10 | 80° C. | 80 | 26.0 | 0.247 | 3.32% | | 16.83% | 62.66% | 14.61% | 77.27% |
| 7 - 2 | 233.84 | 1.00 CH2O | 80 | 71.0 | 0.242 | 2.87% | | 19.69% | 73.31% | 12.63% | 85.94% |
| 7 - 3 | 228.66 | | 80 | 119.0 | 0.236 | 2.42% | | 19.79% | 73.68% | 10.65% | 84.33% |
| 7 - 4 | 223.62 | | 80 | 160.0 | 0.231 | 2.31% | | 20.21% | 75.24% | 10.16% | 85.41% |
| 7 - 5 | 218.59 | | 80 | 208.0 | 0.226 | 1.99% | | 20.36% | 75.80% | 8.76% | 84.56% |
| 7 - 6 | 213.40 | | 80 | 260.0 | 0.220 | 1.88% | | 20.24% | 75.36% | 8.27% | 83.63% |
| 7 - 7 | 207.57 | | 80 | 1291.0 | 0.214 | 0.51% | | 19.85% | 73.90% | 2.24% | 76.15% |
| 7 - 8 | 127.47 | | boiled | | 0.217 | 0.94% | 1.80% | 30.58% | 72.60% | 2.51% | 75.11% |
| 8 - 0 | 239.10 | 1.9NaOH/1EDDA | 50 | 0.0 | 0.247 | 22.73% | | 0.00% | 0.00% | 100.00% | 100.00% |
| 8 - 1 | 239.10 | 50° C. | 50 | 35.0 | 0.247 | 1.89% | | 20.44% | 76.10% | 8.32% | 84.42% |
| 8 - 2 | 233.30 | 1.05 CH2O | 50 | 117.0 | 0.241 | 1.29% | | 22.46% | 83.62% | 5.68% | 89.30% |
| 8 - 3 | 228.81 | | 50 | 160.0 | 0.236 | 1.07% | | 23.18% | 86.30% | 4.71% | 91.01% |
| 8 - 4 | 223.96 | | 50 | 210.0 | 0.231 | 0.82% | | 23.29% | 86.71% | 3.61% | 90.32% |
| 8 - 5 | 218.87 | | 50 | 297.0 | 0.226 | 0.56% | | 24.16% | 89.95% | 2.46% | 92.42% |
| 8 - 6 | 199.40 | | 50 | 1261.0 | 0.206 | 0.24% | | 24.96% | 92.93% | 1.06% | 93.99% |
| 8 - 7 | 141.00 | | boiled | | 0.206 | 0.27% | 1.10% | 35.02% | 94.71% | 0.84% | 95.55% |
| 9 - 0 | 241.10 | 2.1NaOH/1EDDA | 50 | 0.0 | 0.247 | 22.54% | | 0.00% | 0.00% | 100.00% | 100.00% |
| 9 - 1 | 241.10 | 50° C. | 50 | 30.0 | 0.247 | | | 9.07% | 34.05% | 0.00% | 34.05% |
| 9 - 2 | 235.44 | 1.00 CH2O | 50 | 112.0 | 0.241 | 2.71% | 0.60% | 16.04% | 62.17% | 12.02% | 74.19% |
| 9 - 3 | 230.22 | | 50 | 168.0 | 0.236 | 2.10% | 0.70% | 18.36% | 71.21% | 9.32% | 80.52% |
| 9 - 4 | 225.60 | | 50 | 211.0 | 0.231 | 1.55% | 1.10% | 19.28% | 75.96% | 6.88% | 82.84% |
| 9 - 5 | 220.60 | | 50 | 250.0 | 0.226 | 1.02% | 1.20% | 20.77% | 81.88% | 4.53% | 86.41% |
| 9 - 6 | 214.87 | | 50 | 1380.0 | 0.220 | 0.89% | 3.30% | 20.16% | 86.42% | 3.95% | 90.37% |
| 9 - 7 | 112.00 | | boiled | | 0.223 | 1.51% | 9.60% | 34.28% | 82.36% | 3.45% | 85.81% |
| 10 - 0 | 241.10 | 2.1NaOH/1EDDA | 80 | 0.0 | 0.247 | 22.54% | 0 | 0.00% | 0.00% | 100.00% | 100.00% |
| 10 - 1 | 241.10 | 80° C. | 80 | 30.0 | 0.247 | 3.82% | 0.70% | 19.28% | 74.66% | 16.95% | 91.61% |
| 10 - 2 | 236.36 | 1.05 CH2O | 80 | 88.0 | 0.242 | 3.42% | 0.60% | 19.50% | 75.16% | 15.17% | 90.33% |
| 10 - 3 | 231.84 | | 80 | 133.0 | 0.238 | 3.32% | 0.80% | 20.04% | 77.84% | 14.73% | 92.57% |
| 10 - 4 | 226.84 | | 80 | 196.0 | 0.232 | 2.99% | 0.50% | 17.77% | 68.34% | 13.27% | 81.61% |
| 10 - 5 | 221.45 | | 80 | 240.0 | 0.227 | 3.21% | 0.70% | 20.42% | 78.94% | 14.24% | 93.18% |
| 10 - 6 | 216.41 | | 80 | 293.0 | 0.222 | 3.09% | 0.01% | 19.99% | 75.07% | 13.71% | 88.78% |
| 10 - 7 | 210.56 | | 80 | 1290.0 | 0.216 | 2.16% | 1.00% | 19.30% | 75.71% | 9.58% | 85.30% |
| 10 - 8 | 138.64 | | boiled | | 0.218 | 3.22% | 2.50% | 28.68% | 75.34% | 9.29% | 84.63% |
| 11 - 0 | 263.10 | 3.1NaOH/EDDA | 35 | 0.0 | 0.247 | 20.65% | 0.00% | 0 | 0.00% | 100.00% | 100.00% |
| 11 - 1 | 263.10 | 35° C. | 35 | 35.0 | 0.247 | 8.47% | | 2.37% | 9.71% | 41.01% | 50.72% |
| 11 - 2 | 258.10 | 1.00 CH2O | 35 | 72.0 | 0.242 | | | 4.89% | 20.03% | 0.00% | 20.03% |
| 11 - 3 | 252.90 | | 35 | 143.0 | 0.237 | 7.21% | | 6.40% | 26.22% | 34.91% | 61.13% |
| 11 - 4 | 247.40 | | 35 | 182.0 | 0.232 | 7.20% | 0.60% | 6.81% | 30.03% | 34.86% | 64.89% |
| 11 - 5 | 242.74 | | 35 | 221.0 | 0.228 | 6.89% | 0.70% | 8.25% | 36.28% | 33.36% | 69.64% |
| 11 - 6 | 238.43 | | 35 | 257.0 | 0.224 | 6.60% | 1.10% | 9.49% | 42.78% | 31.96% | 74.74% |
| 11 - 7 | 233.63 | | 35 | 1360.0 | 0.219 | 2.88% | 12.00% | 9.08% | 79.81% | 13.94% | 93.75% |
| 11 - 8 | 140.00 | | boiled | | 0.222 | 4.22% | 34.30% | 5.27% | 84.89% | 12.10% | 96.98% |
| 12 - 0 | 263.10 | 3.1NaOH/EDDA | 50 | 0.0 | 0.247 | 20.65% | 0.00% | 0.00% | 0.00% | 100.00% | 100.00% |
| 12 - 1 | 263.10 | 50° C. | 50 | 13.0 | 0.247 | 6.20% | 0.40% | 12.39% | 52.18% | 30.02% | 82.20% |
| 12 - 2 | 257.27 | 1.00 CH2O | 50 | 54.0 | 0.242 | 6.04% | 1.80% | 11.35% | 52.89% | 29.24% | 82.13% |
| 12 - 3 | 251.81 | | 50 | 90.0 | 0.236 | 4.84% | 3.50% | 12.49% | 63.60% | 23.43% | 87.03% |
| 12 - 4 | 247.54 | | 50 | 147.0 | 0.232 | 4.22% | 4.90% | 12.90% | 70.25% | 20.43% | 90.68% |
| 12 - 5 | 243.10 | | 50 | 1237.0 | 0.228 | 3.47% | 15.90% | 8.07% | 89.52% | 16.80% | 106.32% |
| 12 - 6 | 138.80 | | boiled | | 0.231 | 5.50% | 40.00% | 5.45% | 92.71% | 15.02% | 107.73% |
| 13 - 0 | 271.10 | 3.5NaOH/EDDA | 35 | 0.0 | 0.247 | 20.04% | 0.00% | 0 | 0.00% | 100.00% | 100.00% |
| 13 - 1 | 271.10 | 35° C. | 35 | 10.0 | 0.247 | 9.60% | | 4.02% | 16.97% | 47.89% | 64.86% |
| 13 - 2 | 265.99 | 1.00 CH2O | 35 | 47.0 | 0.242 | 7.82% | | 8.07% | 34.07% | 39.01% | 73.08% |
| 13 - 3 | 261.37 | | 35 | 90.0 | 0.238 | 7.31% | | 9.19% | 38.79% | 36.47% | 75.26% |
| 13 - 4 | 256.60 | | 35 | 130.0 | 0.234 | 6.70% | 0.80% | 9.46% | 42.86% | 33.43% | 76.29% |
| 13 - 5 | 252.16 | | 35 | 186.0 | 0.230 | 6.35% | 0.80% | 10.36% | 46.66% | 31.68% | 78.34% |
| 13 - 6 | 246.06 | | 35 | 230.0 | 0.224 | 6.12% | 1.40% | 10.54% | 49.62% | 30.53% | 80.15% |

TABLE 1-continued

| Exp | Tot wt | Comments | temp | t (mins) | Moles EDDA | % EDDANa2 | % ED3ANa3 | % 3KPNa2 | % EDDA to Produc | % Unrxl EDDA | Mass balance |
|---|---|---|---|---|---|---|---|---|---|---|---|
| 13-7 | 241.06 | | 35 | 308.0 | 0.220 | 6.16% | 2.30% | 10.43% | 52.44% | 30.73% | 83.18% |
| 13-8 burned | 235.25 | | 35 | 1320.0 | 0.214 | 2.52% | 13.90% | 6.98% | 80.32% | 12.57% | 92.89% |
| 14-0 | 443.96 | 1.8NaOH/EDDA | 65 | 13.0 | 0.491 | | | 5.38% | 18.71% | 0.00% | 18.71% |
| 14-1 | 442.63 | 65° C. | 65 | 49.0 | 0.490 | | | 10.48% | 36.45% | 0.00% | 36.45% |
| 14-2 | 440.98 | 1.00 CH2O | 65 | 107.0 | 0.488 | | | 16.17% | 56.23% | 0.00% | 56.23% |
| 14-3 | 439.19 | | 65 | 1063.0 | 0.486 | | | 21.12% | 73.45% | 0.00% | 73.45% |
| 15-0 | 448.82 | 1.9NaOH/1EDDA | 50 | 25.0 | 0.491 | | | 2.05% | 7.21% | 0.00% | 7.21% |
| 15-1 | 447.52 | 50° C. | 50 | 85.0 | 0.490 | | | 7.06% | 24.82% | 0.00% | 24.82% |
| 15-2 | 446.05 | 1.05 CH2O | 50 | 122.0 | 0.488 | | | 9.97% | 35.05% | 0.00% | 35.05% |
| 15-3 | 444.25 | | 50 | 173.0 | 0.486 | | | 13.01% | 45.74% | 0.00% | 45.74% |
| 15-4 | 443.14 | | 50 | 1238.0 | 0.485 | | | 25.10% | 88.25% | 0.00% | 88.25% |
| 15-5 | 441.95 | | 50 | | 0.485 | | | 25.52% | 89.48% | 0.00% | 89.48% |
| 16-0 | 450.68 | 1.9NaOH/1EDDA | 65 | 10.0 | 0.491 | | | 6.67% | 23.55% | 0.00% | 23.55% |
| 16-1 | 449.03 | 65° C. | 65 | 41.0 | 0.489 | | | 12.47% | 44.02% | 0.00% | 44.02% |
| 16-2 | 447.46 | 1.00 CH2O | 65 | 82.0 | 0.487 | | | 17.76% | 62.70% | 0.00% | 62.70% |
| 16-3 | 446.18 | | 65 | 125.0 | 0.486 | | | 20.24% | 71.45% | 0.00% | 71.45% |
| 16-4 | 444.85 | | 65 | 1080.0 | 0.486 | | | 24.22% | 85.25% | 0.00% | 85.25% |
| 17-0 | 450.70 | 1.9NaOH/1EDDA | 75 | 17.0 | 0.491 | | | 14.87% | 52.50% | 0.00% | 52.50% |
| 17-1 | 449.45 | 75° C. | 75 | 48.0 | 0.490 | | | 20.66% | 72.94% | 0.00% | 72.94% |
| 17-2 | 448.35 | 1.05 CH2O | 75 | 90.0 | 0.488 | | | 24.26% | 85.65% | 0.00% | 85.65% |
| 17-3 | 447.08 | | 75 | 239.0 | 0.487 | | | 24.97% | 88.16% | 0.00% | 88.16% |
| 17-4 | 445.66 | | 75 | 1233.0 | 0.486 | | | 26.24% | 92.64% | 0.00% | 92.64% |
| 17-5 | 407.20 | | boil | boil | 0.486 | | | 26.41% | 85.19% | 0.00% | 85.19% |
| 18-0 | 450.70 | 1.9NaOH/1EDDA | 50° C. | 10.0 | 0.491 | | | 1.36% | 4.80% | 0.00% | 4.80% |
| 18-1 | 449.36 | 50° C. | 50° C. | 88.0 | 0.490 | | | 7.60% | 26.83% | 0.00% | 26.83% |
| 18-2 | 447.82 | 1.00 CH2O | 50° C. | 1365.0 | 0.488 | | | 24.34% | 85.93% | 0.00% | 85.93% |
| 18-3 | 392.30 | | boil | boil | 0.488 | | | 27.84% | 86.10% | 0.00% | 86.10% |
| 19-0 | 446.70 | 1.8NaOH/1EDDA | 50° C. | 41.0 | 0.491 | | | 2.59% | 9.06% | 0.00% | 9.06% |
| 19-1 | 445.33 | 50° C. | 50° C. | 120.0 | 0.489 | | | 8.63% | 30.20% | 0.00% | 30.20% |
| 19-2 | 443.88 | 1.00 CH2O | 50° C. | 164.0 | 0.488 | | | 11.36% | 39.75% | 0.00% | 39.75% |
| 19-3 | 442.48 | | 50° C. | 1400.0 | 0.486 | | | 24.71% | 86.46% | 0.00% | 86.46% |
| 19-4 | 343.20 | | boil | boil | 0.486 | | | 31.79% | 86.28% | 0.00% | 86.28% |
| 20-0 | 446.07 | 1.8NaOH/1EDDA | 50° C. | 60.0 | 0.491 | | | 3.35% | 11.71% | 0.00% | 11.71% |
| 20-1 | 444.76 | 50° C. | 50° C. | 210.0 | 0.490 | | | 13.30% | 46.47% | 0.00% | 46.47% |
| 20-2 | 442.90 | 1.05 CH2O | 50° C. | 300.0 | 0.488 | | | 16.72% | 58.42% | 0.00% | 58.42% |
| 20-3 | 441.42 | | 50° C. | 1250.0 | 0.486 | | | 24.46% | 85.47% | 0.00% | 85.47% |
| 20-4 | 353.40 | | boil | boil | 0.486 | | | 30.81% | 86.19% | 0.00% | 86.19% |
| 21-0 | 446.70 | 1.8NaOH/1EDDA | 65° C. | 16.0 | 0.491 | | | 7.03% | 24.60% | 0.00% | 24.60% |
| 21-1 | 444.89 | 65° C. | 65° C. | 85.0 | 0.489 | | | 17.26% | 60.40% | 0.00% | 60.40% |
| 21-2 | 443.09 | 1.05 CH2O | 65° C. | 175.0 | 0.487 | | | 22.05% | 77.16% | 0.00% | 77.16% |
| 21-3 | 441.24 | | 65° C. | 253.0 | 0.485 | | | 23.83% | 83.38% | 0.00% | 83.38% |
| 21-4 | 439.56 | | 65° C. | 1240.0 | 0.483 | | | 24.40% | 85.38% | 0.00% | 85.38% |
| 21-5 | 380.0 | | boil | boil | 0.483 | | | 24.96% | 75.50% | 0.00% | 75.50% |
| 22-0 | 446.70 | 1.8NaOH/1EDDA | 65° C. | 25.0 | 0.491 | | | 9.99% | 34.96% | 0.00% | 34.96% |
| 22-1 | 444.33 | 65° C. | 65° C. | 110.0 | 0.488 | | | 19.71% | 68.97% | 0.00% | 68.97% |
| 22-2 | 442.74 | 1.00 CH2O | 65° C. | 165.0 | 0.487 | | | 21.34% | 74.67% | 0.00% | 74.67% |
| 22-3 | 441.04 | | 65° C. | 208.0 | 0.485 | | | 21.40% | 74.80% | 0.00% | 74.88% |
| 22-4 | 439.65 | | 65° C. | 1292.0 | 0.483 | | | 23.72% | 83.00% | 0.00% | 83.00% |
| 22-5 | 394.70 | | boil | boil | 0.483 | | | 25.87% | 81.27% | 0.00% | 81.27% |
| 23-0 | 450.70 | 1.9NaOH/1EDDA | 65° C. | 33.0 | 0.491 | | | 11.14% | 39.33% | 0.00% | 39.33% |
| 23-1 | 448.95 | 65° C. | 65° C. | 92.0 | 0.489 | | | 18.65% | 65.84% | 0.00% | 65.84% |
| 23-2 | 447.21 | 1.05 CH2O | 65° C. | 148.0 | 0.487 | | | 21.69% | 76.58% | 0.00% | 76.58% |
| 23-3 | 445.41 | | 65° C. | 230.0 | 0.485 | | | 23.32% | 82.33% | 0.00% | 82.33% |
| 23-4 | 443.77 | | 65° C. | 1276.0 | 0.483 | | | 24.79% | 87.52% | 0.00% | 87.52% |
| 23-5 | 408.62 | | boil | boil | 0.483 | | | 26.43% | 85.92% | 0.00% | 85.92% |

TABLE 2

| Ex | Temp °C. | M CH2O | EDDA:NaOH | final wt | % 3KPNa2 recyclized | moles 3KP | moles after sampling | % conversion recyclized | % 3KPNA2 after stage 1 |
|---|---|---|---|---|---|---|---|---|---|
| 1 | 50.00 | 1.05 | 1.90 | 373.40 | 31.39% | 0.45 | 0.48 | 92.99% | 89.48% |
| 2 | 65.00 | 1.00 | 1.90 | 364.00 | 31.91% | 0.45 | 0.49 | 91.91% | 85.25% |
| 3 | 75.00 | 1.05 | 1.90 | 376.40 | 29.53% | 0.43 | 0.49 | 88.04% | 85.19% |
| 4 | 50.00 | 1.00 | 1.90 | 372.80 | 31.77% | 0.46 | 0.49 | 93.37% | 86.10% |
| 5 | 50.00 | 1.00 | 1.80 | 370.30 | 32.10% | 0.46 | 0.49 | 94.00% | 86.28% |
| 6 | 50.00 | 1.05 | 1.80 | 388.95 | 30.89% | 0.46 | 0.49 | 94.41% | 86.19% |
| 7 | 65.00 | 1.05 | 1.80 | 393.60 | 29.71% | 0.45 | 0.48 | 93.07% | 85.38% |
| 8 | 65.00 | 1.00 | 1.80 | 415.60 | 26.86% | 0.43 | 0.48 | 88.82% | 81.27% |
| 9 | 65.00 | 1.05 | 1.90 | 417.70 | 29.82% | 0.43 | 0.48 | 99.08% | 85.92% |

| Ex | % difference at 1 - recycle | % unopened 3KPNa2 | % ED3ANa3 by titr | % conversion to ED3ANa3 | % total conv. on ED3ANa3 |
|---|---|---|---|---|---|
| 1 | −3.51% | 2.05% | 36.00% | 91.26% | 95.74% |
| 2 | −6.66% | 1.88% | 38.32% | 95.69% | 98.23% |
| 3 | −2.85% | 2.09% | 36.55% | 93.40% | 97.87% |

TABLE 2-continued

| | | | | | |
|---|---|---|---|---|---|
| 4 | −7.27% | 2.17% | 38.16% | 96.58% | 100.67% |
| 5 | −7.72% | 2.28% | 37.50% | 94.27% | 98.99% |
| 6 | −8.22% | 2.69% | 35.39% | 93.45% | 99.10% |
| 7 | −7.69% | 2.85% | 34.13% | 91.20% | 98.76% |
| 8 | −7.55% | 3.00% | 32.54% | 91.81% | 100.56% |
| 9 | −13.16% | 2.43% | 32.10% | 91.03% | 97.70% |

The data demonstrate the both mass balances and conversions to product are excellent. ED3A was measure by copper (II) salt titration, and 3KP was measured by high pressure liquid chromatography (HPLC). The final column in the Table 1 shows the mass balances for stage 3 (the formation of 3KP) of the reaction. The 9th column in Table 2 shows the percent conversion to product based on recyclization. Recyclization was achieved by acidifying a sample of the reaction mass with HCl to a pH of 2.0. These sample were then allowed to stand in an oven at 40° C. overnight an then on a bench at room temperature for 2 days prior to analysis. This technique was employed to verify the titration results, ensuring that all product was recycled to $3KPH_2$. Mass balances are not as good as those that were titrated. and this may be attributed to HPLC error and dilution error, etc.

What is claimed is:

1. A compound represented by the following formula:

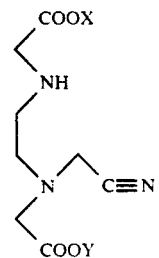

wherein X and Y each represent hydrogen or an alkali metal or alkaline earth metal.

* * * * *